United States Patent [19]

Kowalski et al.

[11] Patent Number: 4,631,687

[45] Date of Patent: Dec. 23, 1986

[54] METHOD AND APPARATUS FOR ANALYSIS EMPLOYING MULTIPLE SEPARATION PROCESSES

[75] Inventors: Bruce R. Kowalski; Gilson H. Rohrback, both of Seattle, Wash.

[73] Assignee: Rohrback Technology Corporation, Seattle, Wash.

[21] Appl. No.: 548,493

[22] Filed: Nov. 3, 1983

[51] Int. Cl.$^4$ .................... G01N 31/00; G06F 15/46
[52] U.S. Cl. ..................... 364/497; 73/23.1; 73/61.1 C; 364/502
[58] Field of Search ................ 364/497–499, 364/502; 73/23.1, 61.1 C, 863.22; 23/306

[56] References Cited

U.S. PATENT DOCUMENTS

| | | | |
|---|---|---|---|
| 3,230,048 | 1/1966 | Skeggs | 23/253 |
| 3,374,659 | 3/1968 | Sanford et al. | 73/23.1 |
| 3,458,285 | 7/1969 | Hrdina | 23/230 |
| 3,508,880 | 4/1970 | Hrdina | 23/253 |
| 3,676,649 | 7/1972 | Burk | 73/23.1 |
| 3,726,127 | 4/1973 | Putnam et al. | 73/23.1 |
| 3,847,546 | 11/1974 | Paul | 23/230 |
| 3,847,550 | 11/1974 | Scott et al. | 73/61.1 C |
| 3,923,460 | 12/1975 | Parrott et al. | 73/61.1 C |
| 4,003,243 | 1/1977 | Blu et al. | 73/61.1 C |
| 4,006,350 | 2/1977 | Jokl | 364/497 |
| 4,271,697 | 6/1981 | Mowery, Jr. | 73/61.1 C |
| 4,353,242 | 10/1982 | Harris et al. | 73/23.1 |
| 4,364,263 | 12/1982 | Sankoorikal et al. | 73/61.1 C |
| 4,367,041 | 1/1983 | Webb, Jr. et al. | 73/61.1 C |
| 4,383,433 | 5/1983 | Stacy | 73/23.1 |

OTHER PUBLICATIONS

Sharaf, Muhammad Abdallah and Bruce R. Kowalski, "Quantitative Resolution of Fused Chromatographic Peaks in Gas Chromatography/Mass Spectrometry", *Analytical Chemistry*, 1982, 54, 1291.
Sonnefeld, W. J., W. H. Zoller, W. E. May and S. A. Wise, "On-Line Multidimensional Liquid Chromatographic Determination of Polynuclear Aromatic Hydrocarbons in Complex Samples", *Analytical Chemistry*, 1982, 54, 723–727.
Wold, Svante, "Cross-Validatory Estimation of the Number of Components in Factor and Principal Components Models", *Technometrics*, vol. 20, No. 4, Nov. 1978.
Eastment, H. T. and W. J. Krzanowski, "Cross-Validatory Choice of the Number of Components from a Principal Component Analysis", *Technometrics*, Feb. 1982.
Koskinen, L., "Data Handling in Gas Chromatography", *Trends in Analytical Chemistry*, vol. 1, No. 14, 1982.
Lawton, William H. and Edward A. Sylvestre, "Self Modeling Curve Resolution", *Technometrics*, Aug. 1971.
Rasmussen, Paul, "Identification of Volatile Components of Jackfruit by Gas Chromatography/Mass Spectrometry with Two Different Columns", *Anal. Chem.* 1983, 55, 1331–1335.
Sharaf, Muhammad Abdallah and Bruce R. Kowalski, "Extraction of Individual Mass Spectra from Gas Chromatography–Mass Spectrometry Data of Unseparated Mixtures", *Analytical Chemistry*, 1981, 53, 518.

*Primary Examiner*—Errol A. Krass
*Assistant Examiner*—Kevin J. Teska
*Attorney, Agent, or Firm*—Christensen, O'Connor, Johnson & Kindness

[57] ABSTRACT

A method and apparatus for analyzing an unknown sample to produce information corresponding to individual components of the sample. The information may then be used to identify and quantify the components. The method of the present invention contemplates subjecting the sample to a plurality of separation processes to produce a corresponding plurality of distinct spatial distributions of the sample. The separation processes could include two or more chromatographic processes in which the stationary phases have different separating characteristics. For each distribution, a set of properties (sample set) is determined at a plurality of positions along that distribution. In one embodiment, the set of properties comprises the absorbance of electromagnetic radiation at a plurality of wavelengths. The sample sets for each process are analyzed to determine one or more basic sets capable of representing all the sample sets for that process. Basic sets common to all processes are taken to be estimates of the set of properties for individual components of the sample. Basic sets found for less than all processes are analyzed to determine whether they can be represented by linear combinations of common basic sets, or whether they can be represented as linear combinations of certain known basic sets and a new basic set. In a further embodiment of the invention, all of the sample sets along all of the distributions are analyzed to determine one or more common basic sets.

29 Claims, 18 Drawing Figures

METHOD AND APPARATUS FOR ANALYSIS EMPLOYING MULTIPLE SEPARATION PROCESSES

FIELD OF THE INVENTION

This invention provides a method and apparatus for analyzing an unknown sample to produce information concerning the properties of individual components of the sample. Such information may then be used to identify and quantify the components of the sample.

BACKGROUND OF THE INVENTION

A fundamental goal in analytical chemistry is the identification and quantitative analysis of the individual components in a sample. Identification generally cannot proceed, however, until the individual components have been to some extent physically separated from one another. One of the most widely used separation techniques is chromatography. In a typical chromatographic process, a sample is passed through a tube or column containing a stationary porous medium that has a different affinity for the various components in the sample, so that the components migrate through the column at different rates. Ideally, the components become completely separated prior to emerging or eluting from the column, and can then be identified as pure chemical species by an appropriate detector positioned at the outlet. Unfortunately, complete separation or resolution of the components is the exception rather than the rule. When chromatographic resolution is very poor or nonexistent, the analyst may not even be able to know that a resolution problem exists, since two or more components will migrate at the same rate and thus be detected as if they were a single component. Even when some degree of resolution is achieved, the problem of identifying overlapped components is one that has plagued chromatography since its inception.

The process of identifying individual chemical components once they have been partially or completely separated is commonly termed detection. One common detection method for chromatography employs an optical spectrometer (e.g., ultraviolet, visible or IR) positioned at the downstream end of the chromatographic column. In a single-channel detector, the spectrometer measures the amount of radiation at a particular wavelength absorbed or emitted by the components as they elute from the column past the detector. Even when the components have been completely separated by the chromatographic column, a single-channel detector may not be capable of identifying the components, because absorption at a single wavelength is not a particularly unique identifier or signature of a chemical species. Knowledge of absorption or emission over a range of wavelengths often is a much better identifier, however, and multichannel detectors have therefore been developed that simultaneously measure the absorption or emission of eluting samples at several different wavelengths. Ideally, the components become fully separated in the chromatographic column, and each one is then uniquely identified as it passes the multichannel detector.

Another type of multichannel detector that has been widely used is the mass spectrometer. In mass spectrometry, an unknown sample is converted into an ionized gas and the ions are then separated according to their mass/charge ratios and quantified by an integral ion sensitive detector. Mass spectrometry can be used as a multichannel detection method for chromatography by periodically sampling the eluting components and analyzing the samples with a mass spectrometer to produce measurements of ion current as a function of mass/charge. Ion current and mass/charge are analogous to absorption and wavelength respectively, and mass spectrometry provides comparatively unique signatures of chemical species.

While multichannel detection is an important advance, it does not directly address the problem of resolution. For example, a specific chemical component will migrate through a chromatographic column in a band of significant length. The concentration or distribution of the component within the band can be graphically represented in an idealized way by a Gaussian curve or peak, although deviations from such ideal behavior are very common. If the migration rates of two components A and B are similar, then the components may elute from the column with the trailing section of the A peak overlapping the leading section of the B peak. When these overlapped sections pass the multichannel detector, the resulting signature will be a combination of varying amounts of the pure A and B signatures, and difficult to interpret. The problem may not be serious if the overlap is slight, since there will still be times, before and after the overlapped section, when pure A and B signatures are detected. If the overlap is large, however, mathematical curve resolution may be required to resolve and identify the individual components.

One such curve resolution technique is based on principal component analysis or factor analysis. Factor analysis can be generally understood by imagining that two components have eluted from a chromatographic column at nearly the same time, and that the absorption of light by the overlapped, eluting components has been measured as a function of wavelength at 20 different time points during the interval when the components were passing a multichannel UV-VIS spectrophotometic detector. One now has, in effect, 20 sequential graphs or signatures of absorption versus wavelength. Since the measured absorption is due to two components A and B, then it should be possible to produce all 20 absorbance graphs by adding together, in varying proportions, two underlying graphs corresponding to the signatures of pure A and pure B. In many cases, methods based on factor analysis may be used to process the data represented by the 20 graphs and to find the graphs or signatures corresponding to components A and B, and thus resolving the single chromatographic peak into its separate components.

Prior techniques based on factor analysis are effective only when the components are at least partially separated by chromatography or by other separation techniques. When components elute through a chromatographic column at the same or an immeasurably different rate, however, factor analysis is unable to resolve the composite detection data into individual component signatures. It is quite common, especially in the analysis of complex mixtures, to find that many components have nearly identical migration rates, and no methods have heretofore been available for the analysis of such complex samples in an efficient manner.

SUMMARY OF THE INVENTION

The present invention provides a method and apparatus for analyzing a sample such that data corresponding to its individual components is produced. The power of the technique can be appreciated from the fact that it is capable of resolving a given component even if that component is never separated, to any degree, from other components in the sample.

In one preferred embodiment, the method of the present invention comprises subjecting the sample to be analyzed to a plurality of separation processes adapted to produce a corresponding plurality of different spatial or temporal distributions of the sample. For each distribution, a set of properties (sample set) is determined at a plurality of positions along that distribution, the set of properties being the same for each process. The resulting sample sets for each process are then analyzed to determine one or more basic sets capable of representing all of the sample sets for that process. The basic sets for the different processes are then compared to identify one or more basic sets common to all processes. Such common basic sets are taken to be estimates of the set of properties associated with the individual components making up the sample. Incomplete basic sets found for less than all processes may then be analyzed to determine whether they can be represented by linear combinations of common basic sets, or whether they can be represented as linear combinations of certain known basic sets and a new basic set. Particular embodiments are disclosed in which the separation processes comprise two chromatographic columns having different stationary phases, and the set of properties comprises the absorbance of electromagnetic radiation at a plurality of wavelengths.

An apparatus according to one embodiment of the present invention comprises a plurality of separation means adapted to produce a plurality of different distributions of the sample, detection means for determining sample sets at a plurality of positions along each distribution, and processing means for analyzing the sample sets to determine the common basic sets.

In an additional embodiment of the invention, all of the sample sets determined along all of the distributions are analyzed to determine one or more common basic sets, such that all the sample sets can be represented by the common basic sets.

These and other features of the invention will become apparent in the detailed description and claims to follow, taken in conjunction with the accompanying drawings.

DETAILED DESCRIPTION OF THE INVENTION

Figure 1:
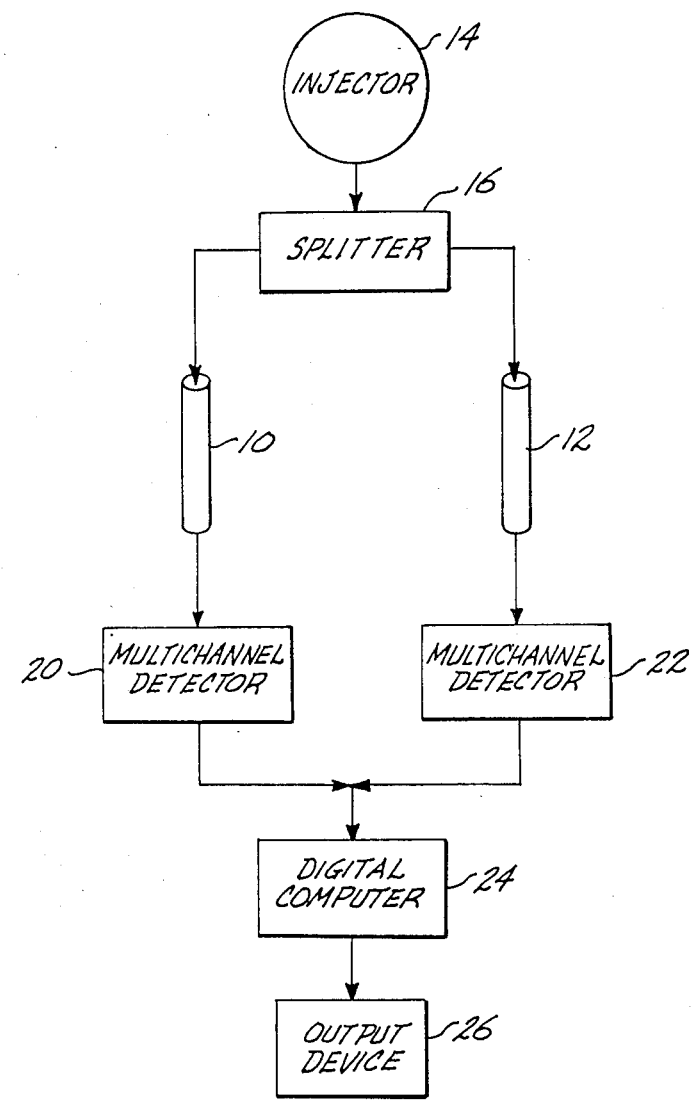
FIG. 1 is a block diagram of a chromatographic apparatus suitable for carrying out the present invention.

The present invention involves the use of two or more separation processes in connection with multichannel detection means. The term "separation process" includes all techniques capable of producing at least a partial separation of the components of a mixed sample. The particular processes selected will depend upon the nature of the sample to be analyzed. Examples of separation processes that may be suitable for a given application include liquid chromatography, gas chromatography, paper chromatography, thin layer chromatography, ion exchange chromatography, electrophoresis, distillation, sublimation, molecular sieves, field flow fractionation, membrane filtration, centrifugation, thermal diffusion, mass spectrometry, and affinity chromatography. The term "separation process" also includes techniques based on altering the detection characteristics of the components over time, e.g., altering spectral properties by application of a magnetic field (Zeeman effect). The processes selected must produce different separations, i.e., distinguishable distributions of the components. The invention will be illustrated herein utilizing two liquid chromatography processes in which the columns exhibit different separating characteristics.

The multichannel detection means that may be used to carry out the present invention include all techniques capable of determining a set (plurality) of properties of individual components in the sample, such that characteristic or identifying signatures of the components can be produced. Examples include multichannel electromagnetic radiation spectroscopy (e.g., UV, visible, IR), in which the absolute intensity or intensity difference of radiation is measured at a plurality of wavelengths, and mass spectrometry, in which ion current is measured at a plurality of mass/charge ratios. Other suitable multichannel detection means include electrochemical methods such as voltammetry and potentiometry, and magnetic resonance techniques such as NMR. The multichannel detection means can also comprise means for determining a set of unrelated properties, such as a single channel spectrometer in combination with other physiochemical measurements. However, the same multichannel detection method, i.e., the same set of properties, must be determined for each separation process. Different measurements could be made for different processes, so long as appropriate means were available for converting the measurements into a single set of properties common to all processes. In the description to follow, the invention will be illustrated using a multichannel ultraviolet spectrophotometer as the multichannel detection means.

In the practice of the present invention, each separation process is used to produce a distribution of the components of the unknown mixture, and the multichannel detection means is then used to generate signatures of the mixture at a plurality of positions along each of the distributions. For many separation processes, e.g., liquid chromatography, this is most conveniently accomplished by arranging for the material eluting from the separation column to flow past a stationary detector, and by having the detector make measurements at a series of times. The following description will illustrate the present invention using multichannel detection measurements made at a plurality of discrete time points, it being understood that this is simply one method of sampling a chromatographic distribution.

FIG. 1 schematically illustrates a chromatographic apparatus that may be used to carry out the present invention. The apparatus comprises two liquid chromatography columns 10 and 12 having different stationary phases selected to produce qualitatively different types of separations of the components to be analyzed. For example, one might choose columns 10 and 12 packed with polar and nonpolar absorbing media respectively. A sample to be analyzed is introduced via injector 14 and flows together with a solvent or mobile phase through splitter 16 into columns 10 and 12. The components of the sample migrate through columns 10 and 12 at various rates, and then elute past multichannel ultraviolet spectrophotometric detectors 20 and 22, respectively. Each detector 20 and 22 measures the absorbance of the solvent/sample mixture at a plurality of wavelengths at each one of a series of evenly spaced time points. The resulting absorbance data is stored and processed by digital computer 24, and the results are communicated to the analyst via an output device 26 such as a CRT screen, plotter, or printer. A suitable instrument for detectors 20 and 22 is the diode array spectrophotometric detector for HPLC, Model No. HP1040A, available from the Hewlett-Packard Company. Suitable instruments for digital computer 24 and output device 26, compatible with the HP1040A detector, are available from the same company.

It should be noted that it is not necessary to perform the two separation processes simultaneously. For example, a single chromatographic column could be used, the sample being injected first using one solvent and then a second time with a different solvent. In this case, a single multichannel detector would suffice. The two-column embodiment of FIG. 1 could also be modified by providing a single multichannel detector having two sample cells and means for switching the optical path back and forth (i.e., multiplexing) between the cells.

Figure 2:
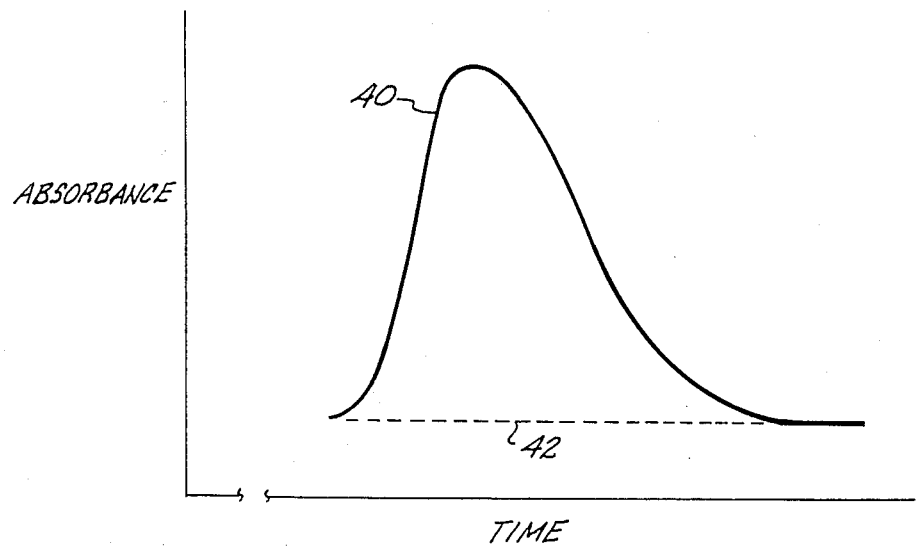
FIG. 2 shows a single absorbance peak such as that produced by a spectrophotometric detector in connection with a chromatographic separation process.
Figure 3:
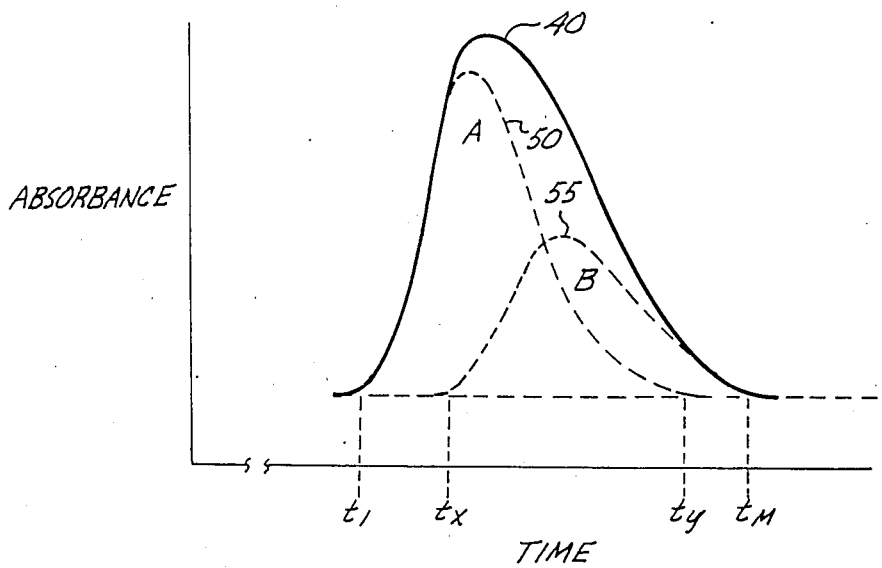
FIG. 3 shows a composite absorbance peak resolved into two components.

For each column 10 and 12, the output of each channel of the multichannel detectors 20 and 22 over time will generally be represented by a series of absorbance peaks separated by periods when no components are detected. FIG. 2 illustrates one such peak 40. The absorbance level 42 before and after peak 40 is termed the background level, and represents principally the absorbance of the solvent mobile phase or sample carrier. The absorbance above background level 42 is due to one or more components of the sample, and the object is to identify such components. A necessary first step is to determine whether peak 40 is due to a single component or to several components that have migrated through the chromatographic column at essentially the same rate. In the latter case, it is then required to resolve composite curve 40 into its separate individual components. FIG. 3 illustrates a hypothetical resolution for the case in which the peak is due to two components A and B, whose individual absorbances 50 and 55 add linearly to produce peak 40.

A number of mathematical techniques have been developed to resolve curves of the type indicated generally in FIG. 3. Some prior methods have assumed that the curve shapes were Gaussian, or have resolved the data by tentatively identifying components A and B, and then testing this assumption to see if previously known curves 50 and 55 could be used to generate curve 40.

Figure 4:
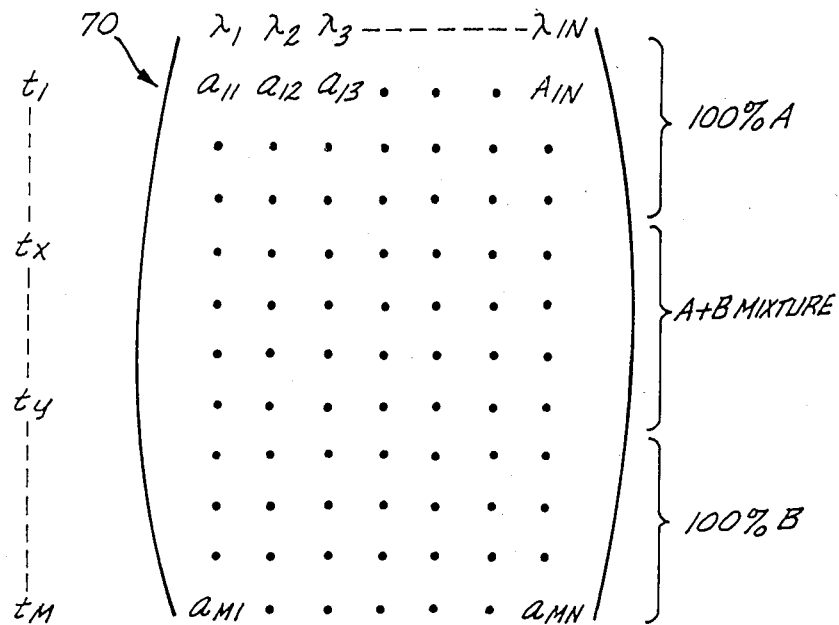
FIG. 4 schematically illustrates a data matrix consisting of a plurality of absorbance measurements.

A different and often superior technique, known as self-modeling curve resolution, is based on factor analysis. To illustrate this technique, assume that a sample has been analyzed using column 10 and detector 20 only, and that FIG. 2 represents the output of one channel of multichannel detector 20. When the data for all channels from detector 20 is collected, it can be arranged as indicated in FIG. 4. In FIG. 4, it is assumed that the UV absorbance of the sample has been measured at N different wavelengths $\lambda_1$ through $\lambda_N$, and that at each wavelength, the absorbance was sampled at M sequential times $t_1$ through $t_M$. In general, this range of times may comprise the entire measurement period, or a subrange as illustrated in FIG. 2. In either case, the optical absorbance at time i and wavelength j is designated $a_{ij}$, and the $a_{ij}$ values are arranged in a data matrix 70 in which each row represents the wavelength spectrum of the unknown at a particular time (i.e., an absorbance spectrum), and each column represents a time spectrum at a particular wavelength (i.e., a wavelength chromatogram). The data represented by curve 40 in FIGS. 2 and 3 would therefore comprise a single column of the FIG. 4 matrix. In the usual case, the background level 42 will be determined for each channel and subtracted from the data, so that the $a_{ij}$ values represent the absorbance of the sample alone.

It will be assumed, as indicated in FIG. 3, that peak 40 represents two components A and B, that component A has eluted from the chromatographic column from times $t_1$ through $t_Y$, and that component B eluted at times $t_X$ through $t_M$, where $t_1 < t_X < t_Y < t_M$. From times $t_1$ through $t_{X-1}$, only component A is measured, and from times $t_{Y+1}$ through $t_M$, only component B is measured. Measurements during the intermediate time interval $t_X$ through $t_Y$ include both components.

Figure 5:
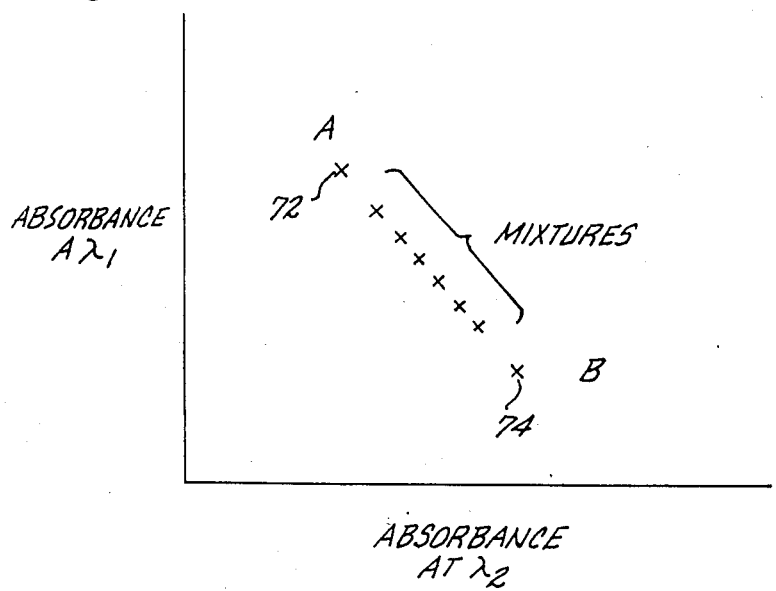
FIG. 5 is a graph of the two-dimensional spectra measured for two partially overlapped components A and B of FIG. 3.

The columns of data matrix 70 can be thought of as points or vectors in an N dimensional space in which the axes are the absorbances at wavelengths $\lambda_1$ through $\lambda_N$. In general, N is chosen to be greater than the maximum number of individual components thought to be present. For purpose of illustration, however, we will assume that N=2. In this case, matrix 70 would have two columns, and each row or spectrum could be represented as a point in a two-dimensional coordinate system. If the spectra were first normalized such that the absorbances in each row summed to unity, the result of plotting the spectra in such a two-dimensional space would be as indicated in FIG. 5. Spectra measured at times $t_1$ through $t_{X-1}$, corresponding to pure component A, would cluster together at point 72, and spectra measured at times $t_{Y+1}$ through $t_M$, corresponding to pure component B, would cluster together at point 74. The clustering is a result of the normalization and the fact that for a pure component, the ratio of absorbance at two different wavelengths is a constant. Spectra measured at $t_X$ through $t_Y$, corresponding to mixtures of A and B, will lie on the straight line between points 72 and 74. For the usual case in which N is greater than 2, the line between points 72 and 74 would be a straight line in an N dimensional space. It should be apparent that if absorbance peak 40 actually corresponded to a single pure component, then the points in FIG. 5 would form a single cluster. On the other hand, if peak 40 were due to three components, then the points in FIG. 5 would lie within the boundaries of a triangle. In general, the space (e.g., line, triangle) containing the spectral points will have a dimension one less than the number of components present.

The two-wavelength illustration of FIG. 5 can be extended and formalized through the use of self-modeling curve resolution. Assume that an N channel detector has been used to record the absorbance of the eluent from a single chromatographic process. If the channels are sampled at M times, then the data can be represented by the $M \times N$ matrix 70 of FIG. 4. The matrix is composed of elements $a_{ij}$ where the first subscript designates the time sample point and the second subscript designates the channel. The entire matrix will be designated by the symbol X. The rows or spectra forming matrix X are normalized such that $$\sum_{j=1}^{N} a_{ij} = 1 \quad \text{for all } i$$

The variance-covariance matrix $X^T X$ formed from this data will have a rank R equal to the number of distinct components present, and it will be possible to represent all of the variance in the data with the R principal eigenvectors $V_1 \ldots V_R$ or $X^T X$. Thus, if two pure components are present, all the spectra in matrix X can be represented as linear combinations of the two principal eigenvectors $V_1$ and $V_2$ of matrix $X^T X$. Stated differently, for two components, it will be possible to rotate the N dimensional spectral space such that all of the spectral points lie on the plane define by eigenvectors $V_1$ and $V_2$. The data can then be represented in a manner to the two-dimensional representation of FIG. 5.

In practice, it is usually preferable to mean-center the data prior to forming the variance-covariance matrix. Mean-centering consists of finding the average value of each column of matrix X, and subtracting that average from each element in that column. The variance-covariance matrix $X^T X$ is then formed by matrix multiplication. Mean-centering thus simply shifts the origin of the coordinate axis to the "center of gravity" of the data points. Its effect is to reduce the rank of the variance-covariance matrix by 1. This can readily be understood with reference to FIG. 5. If the origin of the coordinate system were shifted to a position on the line between points 72 and 74, then all of the variance in the data could be represented by a single eigenvector directed along such line.

Figure 6:
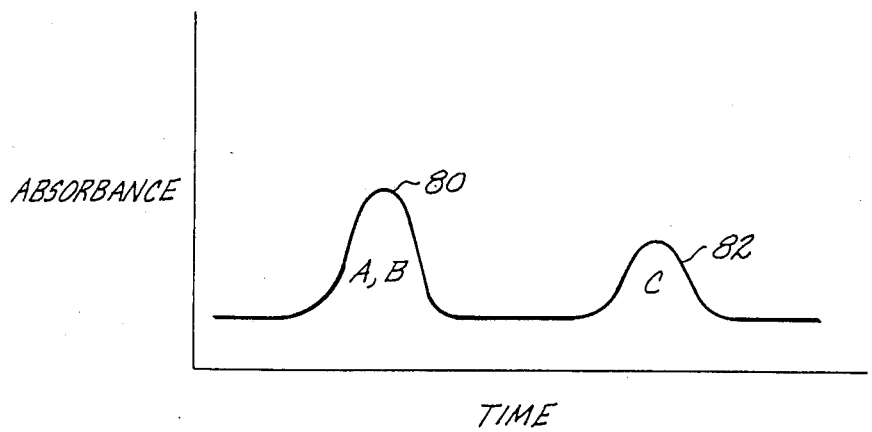
FIG. 6 is a graph of absorbance versus time showing two overlapped components A and B and a third component C.
Figure 7:
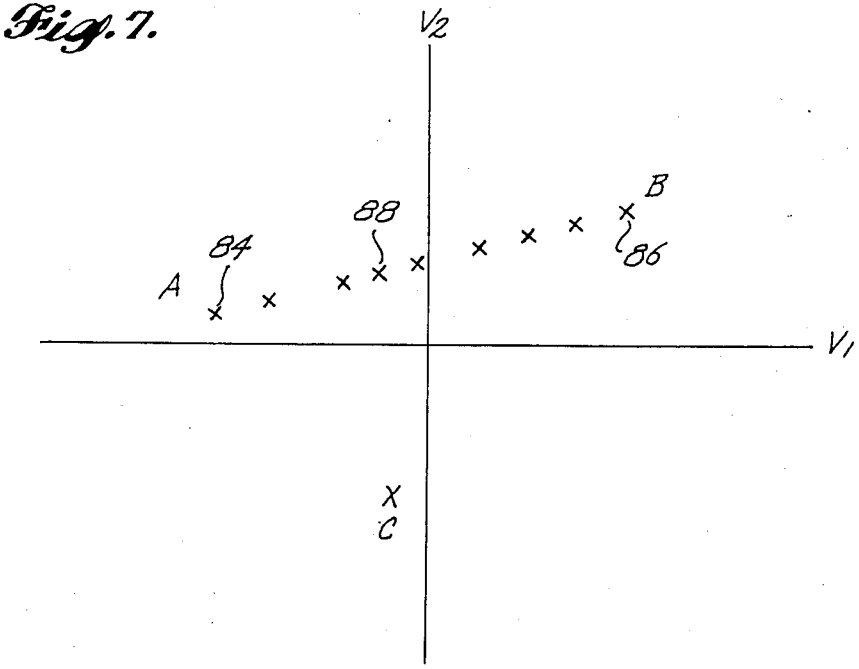
FIG. 7 is a graph, in eigenvector space, of points representing spectra collected for the distribution shown in FIG. 6.

Once the rank and principal eigenvectors corresponding to matrix X have been determined, the spectra can be resolved by projecting each spectral point onto the space defined by the eigenvectors. By way of example, consider the case illustrated in FIG. 6 where the components elute out of a chromatographic column in two groups 80 and 82, with group 80 actually consisting of two components A and B, and group 82 consisting of a single additional component C. If the eluent is measured by a multichannel spectrometer, the resulting data can be represented by a data matrix such as matrix 70 of FIG. 4. After normalization and mean-centering of the data, factor analysis would yield two principal eigenvectors $V_1$ and $V_2$ capable of representing all the variance in the data aside from noise. If all of the spectral points (e.g., rows of matrix 70) are projected onto the plane defined by $V_1$ and $V_2$, the result would appear as in FIG. 7. The points lying above the $V_1$ axis correspond to group 80, and the points lying below the $V_1$ axis correspond to group 82. It is apparent that the latter points form a single cluster, therefore group 82 consists of a single component C. Points from group 80 form a line and therefore represent a mixture of two components A and B. The points 84 and 86 at the two ends of the line between A and B are taken to represent the spectrum of pure A and of pure B, respectively. The fractional compositions represented by the other points (i.e., mixed spectra) on this line, for example point 88, can be determined by measuring the distance between it and points 84 and 86 in a manner analogous to mole fraction diagrams. In particular, the fraction of component A represented by point 88 is equal to the distance between points 86 and 88 divided by the distance between points 84 and 86. Once the fractional amounts of A and B are known for each spectral point, the original chromatographic data can readily be resolved into separate reconstructed chromatograms representative of pure A and pure B. The described self-modeling curve resolution technique thus produces the separate chromatograms without prior assumptions concerning their shapes.

Figure 8:
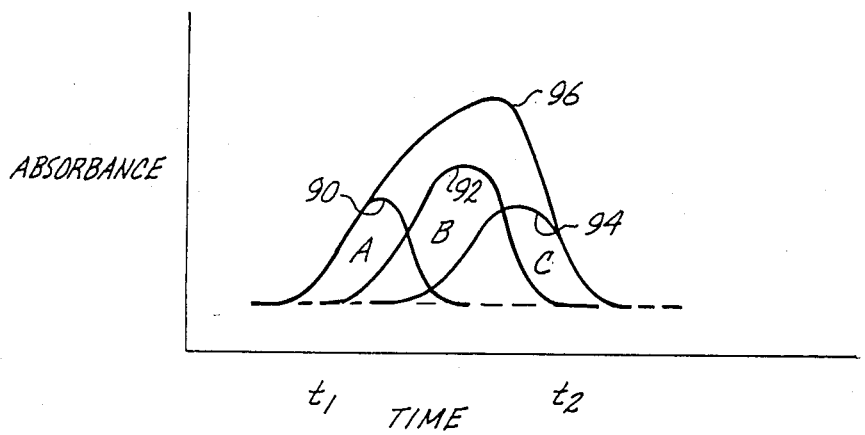
FIG. 8 is a graph showing the absorbance versus time of three partially overlapped components A, B and C.
Figure 9:
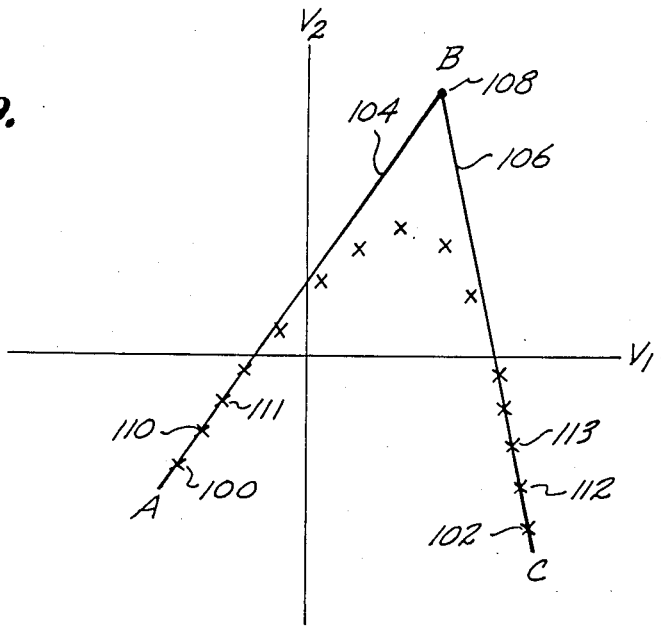
FIG. 9 is a graph, in eigenvector space, of points representing the spectra measured over the distribution shown in FIG. 8.
Figure 10A:
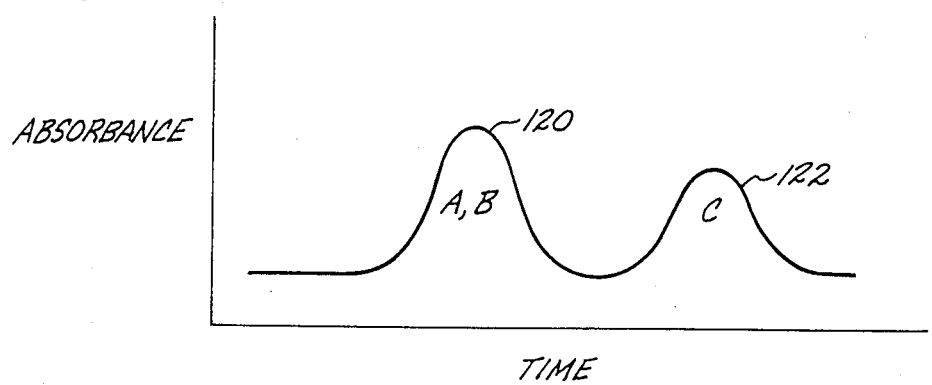
FIG. 10 comprising FIGS. 10A and 10B, consists of two graphs showing the absorbance versus time of three components A, B and C measured on two different separation processes.
Figure 10B:
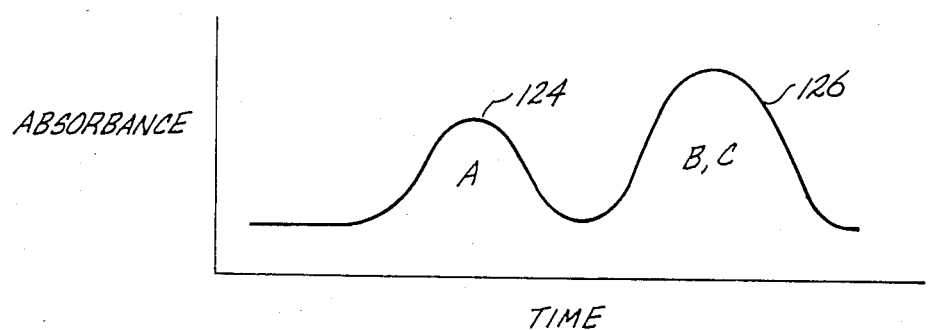

FIGS. 8 and 9 illustrate a more complex case in which three components A, B, and C, represented respectively by curves 90, 92, and 94, have eluted at nearly the same time. Curve 96 represents the data actually measured at one wavelength. While there are times, such as $t_1$ and $t_2$, when pure A and pure C respectively are measured, pure B is never measured. Subjecting the mean-centered multichannel chromatographic data to factor analysis, as described above, would yield two principal eigenvectors corresponding to three pure components. FIG. 9 shows the original spectral data plotted in the spaced defined by principal eigenvectors $V_1$ and $V_2$. While points 100 and 102, corresponding to the spectra of pure A and pure C respectively, can readily be identified, no measured data point corresponds to the spectrum of pure component B. The position of B can, however, be determined by drawing lines 104 and 106 tangent to the data points near points 100 and 102 respectively, and finding the intersection 108. Intersection 108 then corresponds to the spectrum of pure component B. This can be seen by noting that if points near point 100, such as points 110 and 111, were measured before component C began to elute, then B must be on line 104 drawn through such points. Likewise, if points near point 102, such as points 112 and 113, were measured after component A was fully eluted, then B must lie on line 106 drawn through such points. The spectrum of pure component B must therefore lie at the intersection of lines 104 and 106.

The analysis techniques that have been illustrated by FIGS. 6 through 9 may readily be carried out using a digital computer together with known programs for analytic geometry, matrix algebra and curve fitting. They have been shown here in graphical form principally for clarity and ease of illustration.

All of the examples described to this point have involved incomplete overlap (partial separation) between chromatographic peaks, i.e., there were always some times at which pure component spectra could be measured. Complete or virtually complete overlap is quite common, however, particularly for complex mixtures. Further, as overlap becomes more severe, the times during which pure spectra can be measured become shorter, and the signals measured during such times become increasingly dominated by noise. When overlap reaches this stage, traditional analysis techniques break down, and the chemist may not even be aware that a resolution problem exists. For example, as the individual peaks 90, 92, and 94 in FIG. 8 merge together, the corresponding points in FIG. 9 collapse into a single cluster, indistinguishable from that representing a single pure component.

The present invention overcomes these limitations by adding extra dimensions to the analysis. The dimensions are added by subjecting the unknown mixture to two or more different separation processes. The separation processes could be two different chromatographic columns, as illustrated in FIG. 1, or any other separation processes that produce different spatial (or temporal) distributions of the individual components. An appropriate multichannel detection technique is used to determine a set of properties of the unknown sample (a sample set) at a plurality of positions along each distribution. The resulting sample sets for each process are then analyzed to determine a collection of basic sets capable of representing all of the sample sets for that process. The resulting basic sets for the different processes are then compared to determine those basic sets common to all processes. Such common sets are taken to be the sets of properties (i.e., the multichannel signatures) associated with the individual components making up the unknown sample. Incomplete basic sets found for less than all processes are then analyzed to determine whether they can be represented by linear combinations of common basic sets, or whether they can be represented as linear combinations of certain known basic sets and a new basic set.

The invention can be understood for a simple case with reference to FIGS. 1 and 10–12. Assume that a three-component mixture has been passed through columns 10 and 12 of the apparatus of FIG. 1, and that FIGS. 10a and 10b represent the respective elution profiles at a given wavelength. In the first column (FIG. 10a) components A and B are completely overlapped, and the second column (FIG. 10B) components B and C are completely overlapped. If the data from either the first or second column were to be analyzed separately and plotted in eigenvector space, the result would be a graph having two separate clusters of data points, indicating (incorrectly) that the mixture contains two pure components. Stated differently, the mean-centered variance-covariance matrix formed from the data from either column would have rank of 1.

Figure 12:
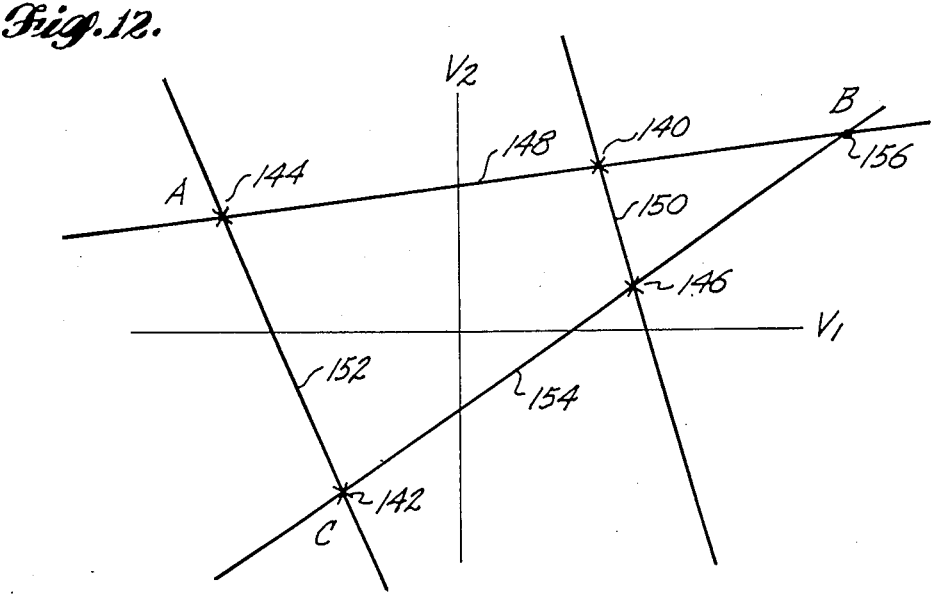
FIG. 12 is a graph, in eigenvector space, of the data represented by FIG. 10.
Figure 11:
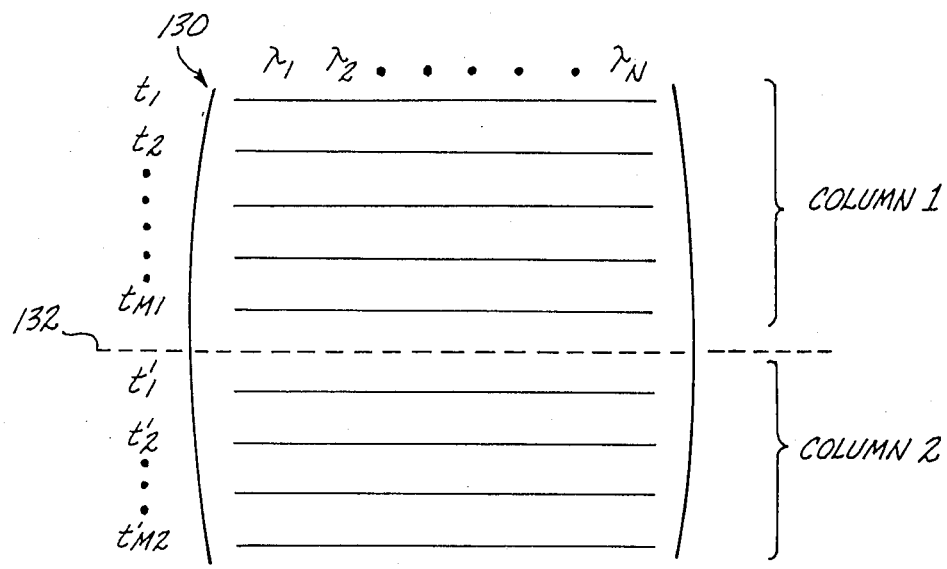
FIG. 11 illustrates the data matrix formed from the absorbances measured for the two separation processes of FIG. 10.

Following the technique of the present invention, however, the data from the two columns is analyzed in a coherent manner. In one embodiment, the spectra from column 10 are combined with the spectra from column 12 to form a single data matrix indicated by numeral 130 in FIG. 11. In FIG. 11, it is assumed that multichannel detectors 20 and 22 (FIG. 1) have analyzed the eluent from columns 10 and 12, respectively, at N wavelengths $\lambda_1$ through $\lambda_N$, the set of wavelengths being the same for the two detectors. Detector 20 performs its measurements at times $t_1 \ldots t_{M1}$, and detector 22 performs its measurements at times $t'_1 \ldots t'_{M2}$. The absorbance data from column 10 can be represented as an $M1 \times N$ matrix $X_1$ in a manner identical to that described for matrix 70 of FIG. 4. In FIG. 11, matrix $X_1$ consists of that portion of matrix 130 above dashed line 132. Similarly, the absorbance data from column 12 can be represented by an $M2 \times N$ matrix $X_2$, corresponding to the portion of matrix 130 below line 132. Utilizing the method of the present invention, the complete matrix 130 is analyzed, by the self-modeling curve resolution technique described above, or by another appropriate technique. Other techniques that are suitable decomposition of three way tables, N-component generalization of self-modeling curve resolution, N-way generalization of Eckhart-Young decomposition, alternating least squares algorithms with optimal scaling features (ALSCOMPS), and methods based on path modeling with latent variables. For the simple case illustrated in FIG. 10, the result could be represented as shown in FIG. 12, wherein the original spectra have been plotted in the plane defined by principal eigenvectors $V_1$ and $V_2$. Spectra from column 10 cluster at points 140 and 142, while spectra from column 12 cluster at points 144 and 146. It may now appear that four components are present in the sample. However, if point 140 represents a pure component Z, then spectra lying at this point should have been found on both columns. The fact that Z (e.g., point 140) was found only on column 10 suggests either that Z was completely overlapped with another component on column 12, that point 140 represents an overlapped combination, or that component Z never emerged from column 12. In the example of FIGS. 10 and 12, the same analysis also applies to points 142, 144, and 146, i.e., none of these spectral points was found on both columns.

The analysis of the data represented by FIG. 12 proceeds in two stages. In the first stage, each point found on only one column is checked to see if it lies on a straight line between two other points found only on the other column. If so, then the point in question represents an overlapped combination of the two other points. In FIG. 12, no points satisfy this criteria, and the analysis therefore proceeds to stage two. In stage two, for each point found on only one column, straight lines are drawn to all points found only on the other column. Thus, in FIG. 12, for point 140, lines 148 and 150 are drawn, and for point 142, lines 152 and 154 are drawn. Identical lines could be constructed for points 144 and 146. All intersections of the lines so drawn are then examined to see if the intersections represent valid spectra. To check validity, the intersection point is transferred back into the original spectral space in which the axes are the absorbances at the various wavelengths. If the transformed point has a negative value (i.e., a negative absorbance) for any axis, it is rejected as invalid.

In FIG. 12, point 156 is the intersection of lines 148 and 154. If point 156 represents a valid spectrum, then point 140 represents the completely overlapped mixture spectrum of the pure component spectra represented by points 144 and 156. These components can be designated A and B, respectively. Proceeding with the analysis, it is then apparent that point 146 represents a mixture spectrum of component B and a third component C whose pure spectrum is represented by point 142. Since the three remaining points 142, 144 and 156 have been "found" on both columns, the actual number of components and their locations have been determined. By transforming points 142, 144 and 156 back to the original spectral axes, the actual spectra representative of pure A, B and C can be produced, and the corresponding components possibly identified by comparison with reference data. The fractional amounts of A, B, and C may be determined for each mixed spectral point by measuring the distances between them and the appropriate pure spectral points as was done for FIG. 7 previously (page 12), or by fitting the pure spectra to the mixture spectra using least squares or another appropriate method. The original chromatographic data is then resolved into separate reconstructed chromatograms representative of pure A, B and C. Each of these reconstructed pure data sets may then be integrated to quantitatively determine the amounts of A, B, and C present, with appropriate reference to known calibration data. It should be noted that this resolution has been achieved even though component B was always completely overlapped or masked by other components of the mixture.

FIGS. 10 and 12 illustrate a three-component case, three being the maximum number of components for which the data can readily be represented in two dimensions. FIGS. 13 through 17 illustrate one preferred method of carrying out the present invention in the more general case in which any number of components may be present. In FIGS. 13 through 17, it is assumed that an unknown sample has been subjected to C different separation processes, and that each spatial distribution has been analyzed at a plurality of positions using the same multichannel detection means. For convenience, the multichannel signatures are termed spectra, although nonspectral detection methods could also be used.

The data from the C processes could be analyzed by combining it into a matrix such as matrix 130 of FIG. 11, and by analyzing the entire matrix using mathematical methods such as those described above. For situations in which there are a large number of components, however, methods based on the direct analysis of matrix 130 can be computationally quite difficult. In addition, since the number of channels in the multichannel detection means must equal or exceed the number of components present, a multicomponent sample can often exceed the capacity of the available multichannel detection means. The method as set forth in FIGS. 13 through 17 avoids this difficulty by taking advantage of the fact that, in most cases, each separation process will separate the components into a series of non-overlapping groups. Since, for a given process, no components will be found in more than one group, the data corresponding to each group can be "preprocessed" using, for example, self-modeling curve resolution and the results then combined and analyzed as described below. The method of FIGS. 13 through 17 will, in general, be carried out on a digital computer, such as computer 24 shown in FIG. 1, and the flow chart of FIGS. 13 through 17 will, in that case, represent the program for operating the computer.

Figure 13:
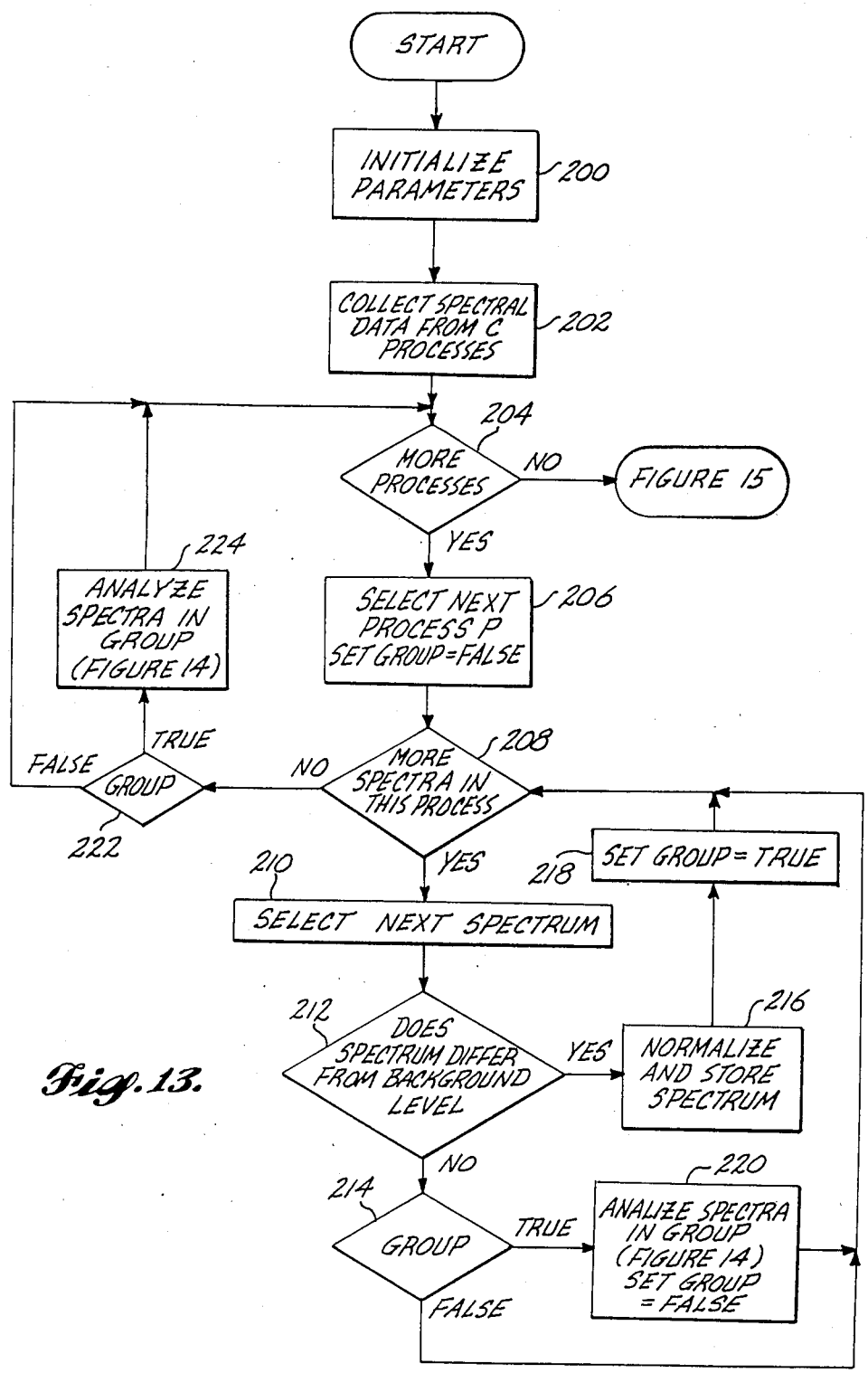
FIGS. 13-17 are flow charts detailing the steps for one preferred method of carrying out the present invention.

Referring to FIG. 13, the program commences by initializing parameters in block 200 and by collecting the spectral data from C processes in block 202, C being greater than 1. If appropriate, the operations in block 202 could include determining the background level for each process, and subtracting such background levels from the collected data.

The data from the several processes are analyzed one at a time, commencing with block 204. As long as there are more processes to be analyzed, control passes from block 204 to block 206, where the next process P is selected and the variable GROUP is assigned a value of false. The program then enters a loop, commencing at block 208, and remains in that loop until all spectra (i.e., all multichannel signatures) in process P have been analyzed. The next spectrum to be analyzed is selected by block 210, and block 212 determines whether this spectrum differs from the background level for process P. If not, and if GROUP is still false, the program loops back to block 208. When a spectrum differing from the background level is found in block 212, control passes to block 216, where the spectrum is normalized and stored. The variable GROUP is then assigned a value true in block 218, and control returns to block 208. When the end of a data group is reached, the test in block 212 fails, and block 214 then passes control to block 220, wherein the data in the group are preprocessed as described below. When preprocessing is complete, GROUP is set to false, and control returns to block 208.

When all spectra for process P have been analyzed, the test in block 208 fails, and control passes to block 222. If the last spectra measured on process P was part of a group (as opposed to a background level measurement), then this final group for process P is preprocessed in block 224. Control then returns to block 204. If there are more processes to be analyzed, the program proceeds to do so, commencing again with block 206. Otherwise, control passes to the program portion commencing with FIG. 15.

Figure 14:
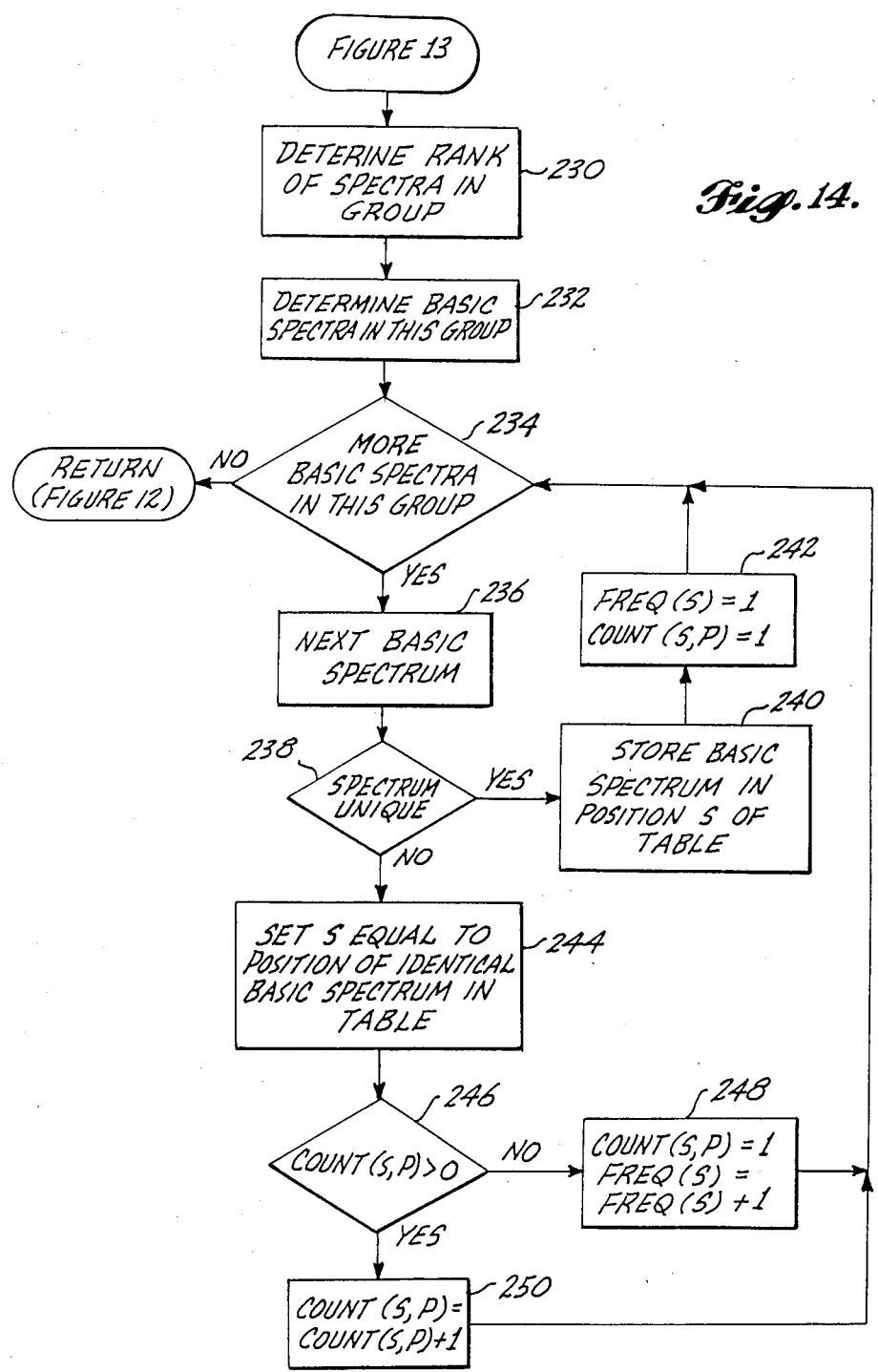

FIG. 14 sets forth the subprogram used to process the spectra comprising a group. The rank of the spectra in the group is first determined in block 230, and the data is then resolved into one or more basic spectra in block 232. The rank of the data is preferably determined by means of the self-modeling curve resoluton techniques previously described. If the rank of the mean-centered data is zero, then the one basic set is the mean of the spectra in the group. If the rank is greater than zero, then the basic sets are determined by self-modeling curve resolution or by another appropriate technique. The result will be that for each group, the basic sets will be the minimum number of linearly independent spectra capable of representing all spectra in the group, i.e., it will be possible to express each spectrum in the group as a linear combination of that group's basic spectra. The basic spectra correspond either to pure components, or to overlapped mixtures that cannot be resolved by the separation process. Basic spectra may also be used as described previously to calculate the reconstructed chromatograms for pure components which can then be integrated and used to calculate concentrations.

Once the basic spectra for a group have been determined, they are compared to basic spectra for other groups beginning with block 234. The subprogram of FIG. 14 keeps track of basic spectra found for different groups and processes by means of a spectrum table and related program variables FREQ and COUNT. Each unique basic spectra found for any process is stored in the spectrum table. For each spectrum table entry S, FREQ(S) indicates the number of different processes for which entry S has been found, and COUNT (S, P) indicates the number of times (usually 0 or 1) that entry S has been found on process P.

The program executes a loop beginning with block 234 for each basic spectra in the group presently being analyzed. Block 236 selects the next basic spectrum in the group, and block 238 determines whether it is identical to any basic spectrum already found and stored in the spectrum table. If the basic spectrum is unique, then block 240 stores it in position S (the next available position) in the spectrum table. Block 242 then initializes the FREQ and COUNT variables for spectrum S and returns control to block 234. If a basic spectrum is found by block 238 to be the same spectrum already in the spectrum table, block 244 sets variable S so that it points to such spectrum table entry. Block 246 then tests to see whether basic spectrum S has already been found on the current process P. If not, then the COUNT and FREQ variables are initialized or incremented, as indicated in block 248, and control returns to block 234. If basic spectrum S has already been found on process P, then the COUNT variable corresponding to S and P is incremented, as shown in block 250, and the program then loops back to block 234. When all basic spectra in the current group have been analyzed, then the test in block 234 fails and the program flow returns to FIG. 13.

Figure 15:
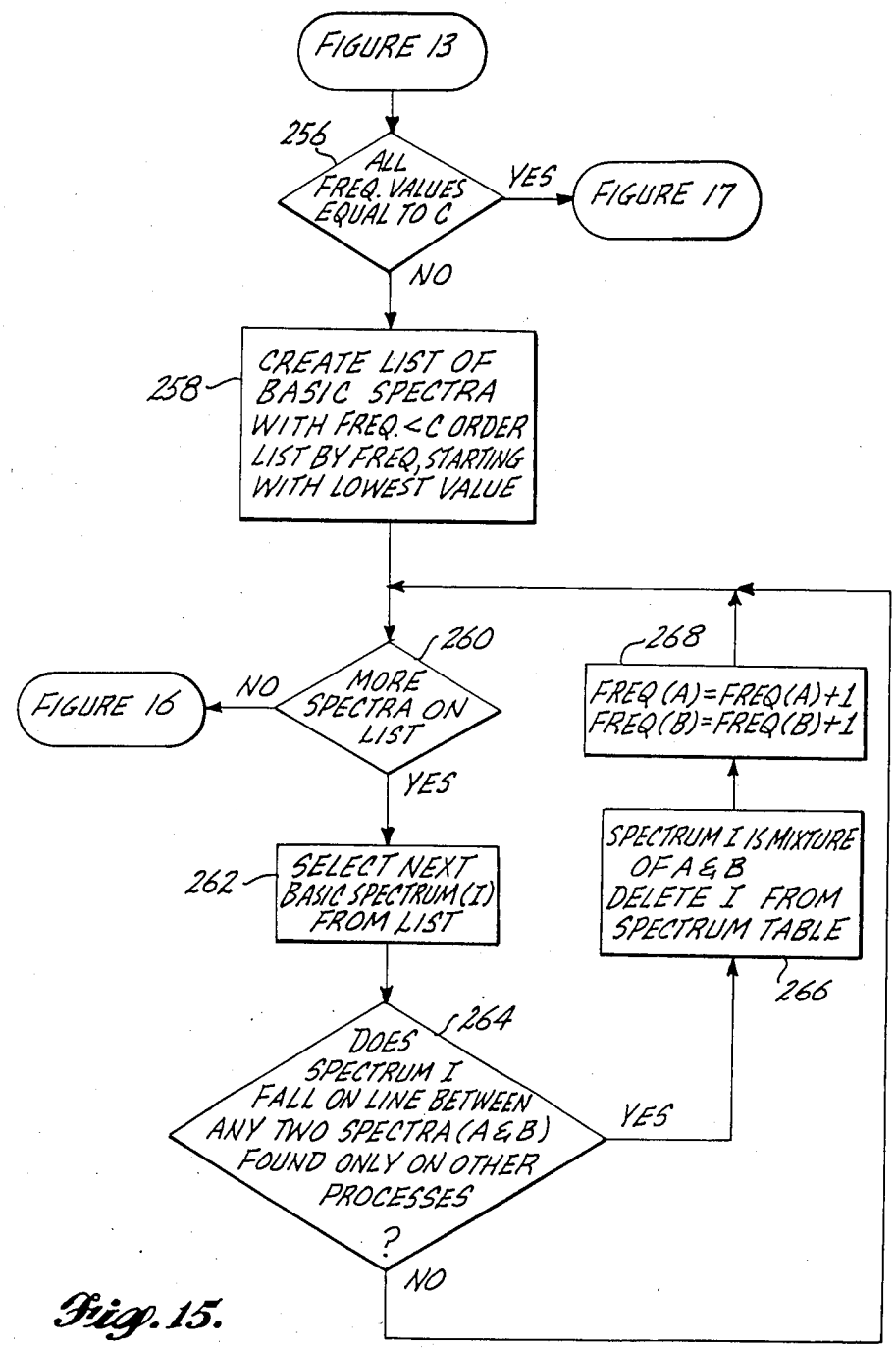

When all spectra from all processes have been analyzed, control passes from block 204 (FIG. 13) to block 256 of FIG. 15. At this point, the spectrum table contains a number of basic spectra, each of which represents either a pure component spectra, or an overlapped combination of spectra which could not be resolved in blocks 230 and 232. The counter array FREQ indicates, for each basic spectrum, the number of processes on which that particular basic spectrum was found. If all FREQ values are equal to C, then each basic spectrum was found on all processes, and the analysis is complete. In this case, the test in block 256 is successful, and control passes to FIG. 17. However, if all FREQ values are not equal to C, then some of the basic spectra in the spectrum table were found on some processes but not others. For a process such as chromatography, one possible explanation is that some components were completely retained in one or more columns, and therefore never detected. Another possible explanation is that some of the basic spectra actually represent overlapped combinations of pure spectra. This second possibility is analyzed by the program beginning at block 258. Block 258 creates an ordered list of all basic spectra found less than C times, the list beginning with those basic spectra found least frequently. The program then enters a loop beginning with block 260 which analyzes each basic spectrum in the list to determine whether it in fact consists of a linear combination of two other basic spectra. In particular, block 262 selects the next basic spectrum (I) from the list, and block 264 then determines whether basic spectrum I lies on a straight line between any two other basic spectra (A and B) that were found only on other processes. If basic spectrum I cannot be so resolved, then the program returns to block 260 and continues looping. If the test in block 264 is satisfied for two basic spectra A and B, then basic spectrum I actually represents an overlapped combination of the components corresponding to basic spectra A and B. Basic spectrum I is therefore deleted from the spectrum table in block 266, the FREQ values for A and B are incremented in block 268, and control returns to block 260. The line referred to in block 264 is a line drawn in N dimensional spectral space, where N is the number of channels in the multichannel detector.

Figure 16:
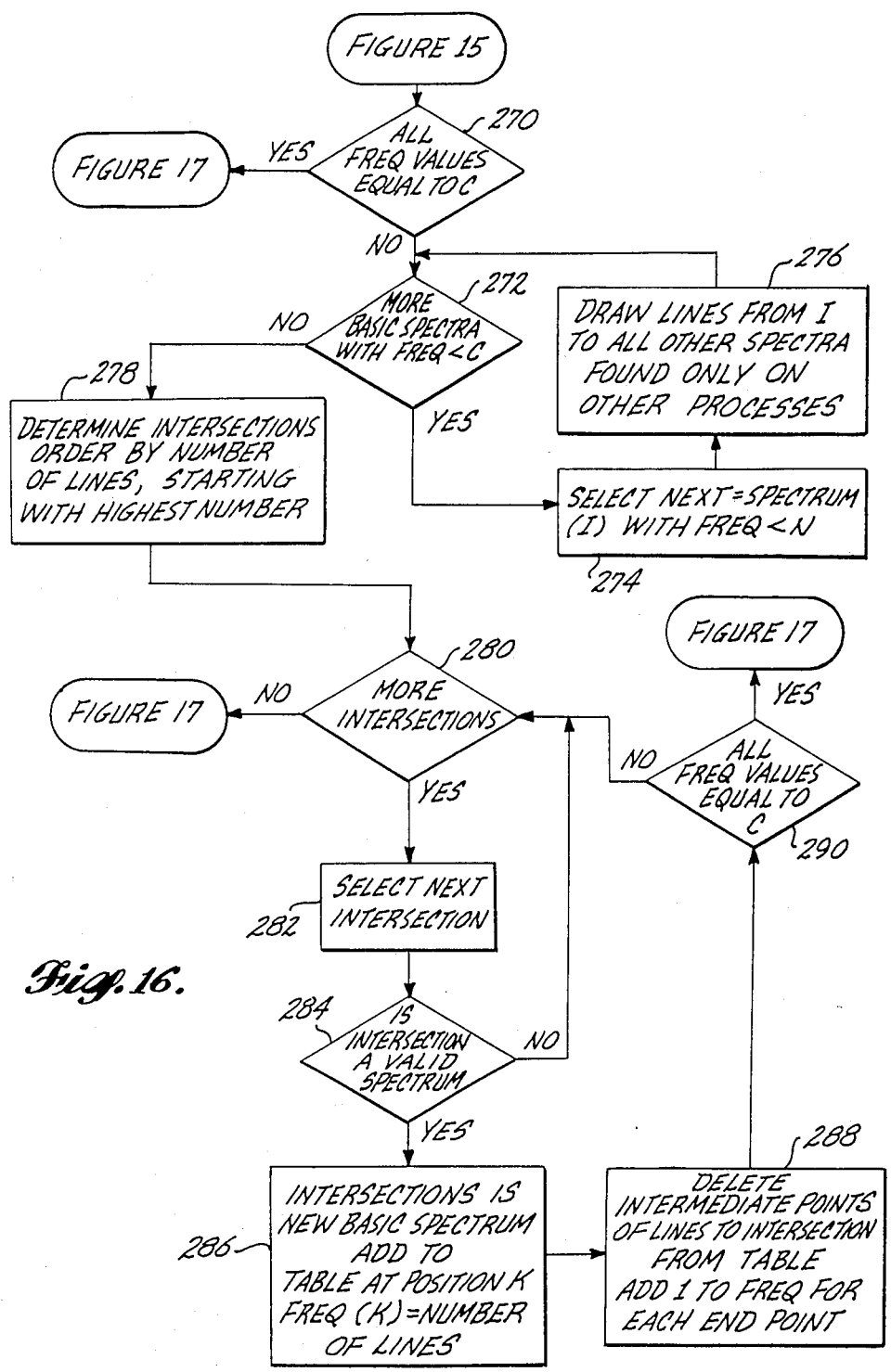
Figure 17:
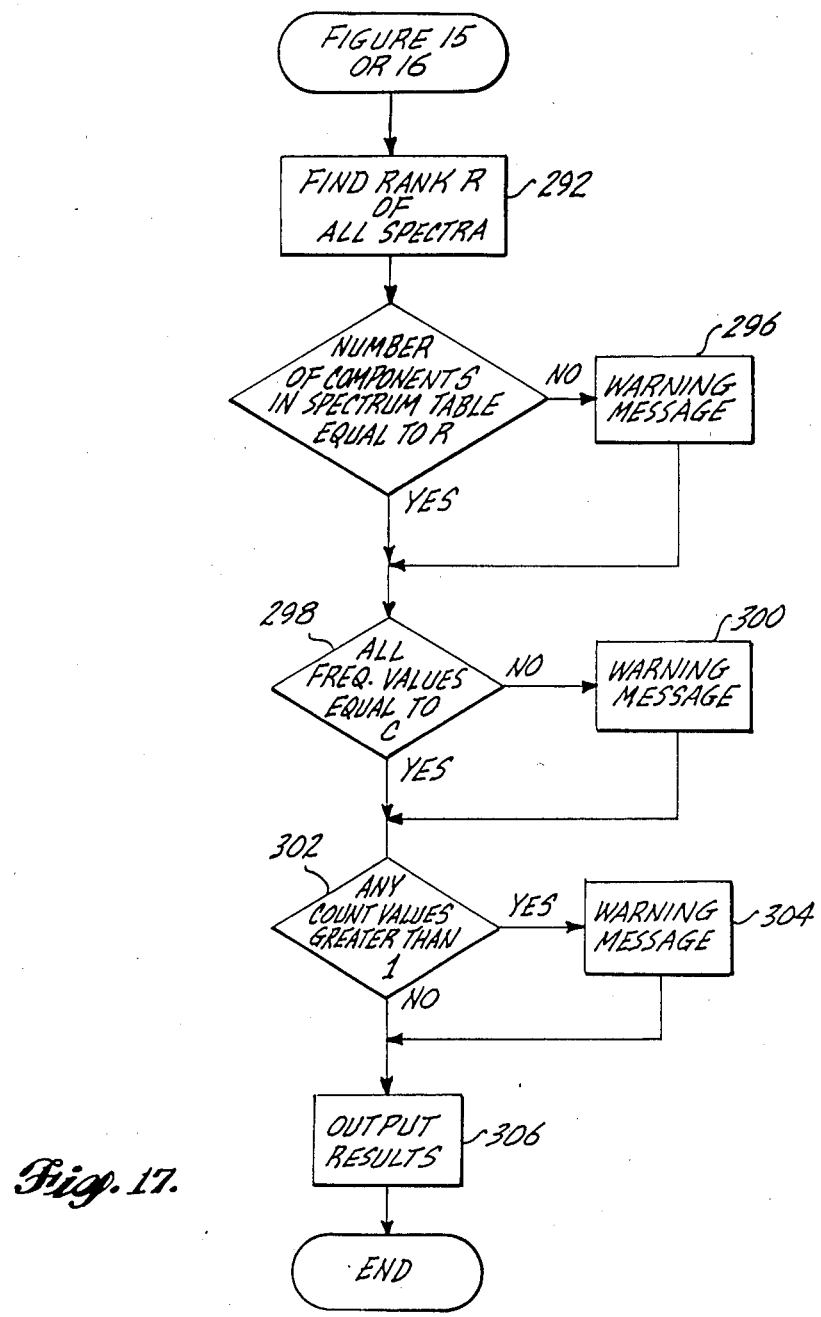

When all the basic spectra on the list created in block 258 have been processed, then control passes from block 260 to block 270 of FIG. 16. In block 270, the FREQ values are again tested to see whether all basic spectra have been found on all processes. If so, then the resolution process of FIG. 15 has been successful, and control jumps to FIG. 17. If not, then the analysis enters a second stage commencing with block 272. This second stage corresponds to the simplified example illustrated in FIG. 12. In the loop formed by blocks 272, 274 and 276, straight lines are drawn from each basic spectra found less than C times to all other basic spectra found only on other processes. When all such lines have been drawn, block 278 determines all of the intersections of such lines. As with the analysis illustrated in FIG. 15, the lines drawn by block 276 are straight lines in N dimensional spectra space.

Each intersection determined by block 278 will have two or more lines radiating from it. The intersections are ordered based on the number of radiating lines, beginning with those with the greatest number. The program then enters a loop beginning at block 280 in which each intersection is analyzed. Block 282 selects the next ordered intersection, and block 284 determines whether this intersection corresponds to a valid spectrum. This determination is made by checking the validity of each coordinate of the intersection point. For example, for an N channel spectrophotometric detector in which the measured data represents absorbances, each of the N coordinates of the intersection point is chekced to see if it is a positive number. If an intersection does not represent a valid spectrum, then the program returns to block 280 and continues looping. If an intersection is valid, then the intersection represents a new pure component, and a basic spectrum corresponding to the intersection is added to the spectrum table as indicated in block 286. The FREQ value for this new basic spectrum is set equal to the number of lines radiating from the intersection. In block 288, for each line radiating from the intersection, the basic spectrum corresponding to the intermediate point of the line is deleted from the spectrum table, and the FREQ value for the basic spectrum on the other end of the line is incremented by one. The program then checks, in block 290, to see whether all basic spectra have been found on all processes. If not, then it resumes checking intersections at block 280. When test 290 has been satisified or when all intersections have been checked, control passes to block 292 of FIG. 17.

Block 292 finds the rank of the data matrix formed from the spectra from all processes. For a two-process case, R would be the rank of matrix 130 in FIG. 11. Block 294 then checks to see whether the number of basic spectra in the spectrum table equals R. If it is not, then a warning message is printed in block 296. Block 298 then checks to see whether all basic spectra have been found on all processes. If they have not, then a warning message is printed in block 300. Block 302 then checks to see if the COUNT variable is greater than 1 for any basic spectrum and process. If so, then it is possible that the sample being analyzed contains two components having identical signatures, and a warning message is printed in block 304. Finally, in block 306, the basic spectra stored in the spectrum table are output via output device 26 (FIG. 1), and the program is then complete.

While the preferred embodiments of the invention have been illustrated and described herein, it should be understood that variations will be apparent to those skilled in the art. Accordingly, the invention is not to be limited to the specific embodiments illustrated and described herein and the true scope and spirit of the inven- The embodiments of the invention in which an exclusive property or privilege is claimed are defined as follows:

1. A method for analyzing a sample in order to produce data corresponding to a set of properties of at least one of the individual components thereof, the properties being selected such that said set of properties is adequate for identifying at least one of said components, said method comprising the steps of:
   subjecting said sample to a plurality of separation processes, the separation processes being adapted to produce a corresponding plurality of different distributions of the sample;
   determining said set of properties of the sample, to produce a corresponding sample set, at each of a plurality of positions along each of said distributions;
   determining one or more basic sets for each separation process, such that all sample sets corresponding to the distribution produced by that process can be represented by the basic sets for that process; and
   comparing the basic sets for the different processes with one another to thereby identify one or more common basic sets such that all of the sample sets can be represented by the common basic sets, whereby said common basic sets are estimates of said set of properties for individual components.

2. The method of claim 1, wherein the plurality of separation processes comprises two chromatographic processes having different stationary phases.

3. The method of claim 2, wherein said set of properties comprises the absorbance of electromagnetic radiation at a plurality of wavelengths.

4. The method of claim 1, wherein comparing the basic sets comprises finding a new basic set such that there exists a plurality of first basic sets such that, for each first basic set, a second basic set not found for any process for which said first basic set was found can be represented as a linear combination of said first basic set and said new basic set.

5. The method of claim 1, wherein comparing the basic sets further comprises identifying one or more incomplete basic sets found for less than all processes, and for each incomplete basic set, determining whether said incomplete basic set can be represented as a linear combination of two basic sets not found for any processes for which said incomplete basic set was found and, if it can be so represented, for each process for which said incomplete basic set was found, deleting said incomplete basic set and adding said two basic sets.

6. The method of claim 5, wherein said incomplete basic sets are analyzed in ascending order based upon the number of processes for which they were found.

7. The method of claim 5, wherein comparing the basic sets further comprises finding a new basic set such that there exists a plurality of first basic sets such that for each first basic set, a second basic set not found for any process for which said first basic set was found can be represented as a linear combination of said first basic set and said new basic set.

8. The method of claim 1, 5, 4 or 7, wherein determining the basic sets further comprises normalizing each sample set such that it sums to a constant value.

9. The method of claim 8, wherein determining the basic sets for each separation process further comprises, for each group of one or more components fully separated from the other components by that process, analyzing the sample sets corresponding to said group to determine the number of components in said group and the basic sets for said group, such that all sample sets corresponding to said group can be represented by the basic sets for said group.

10. The method of claim 9, wherein analyzing the sample sets corresponding to said group comprises performing a self-modeling curve resolution analysis on the sample sets corresponding to said group such that said group is resolved into one or more basic sets.

11. The method of claim 10, wherein analyzing the sample sets corresponding to said group further comprises mean-centering the data corresponding to each of said properties prior to performing the self-modeling curve resolution analysis.

12. A method for analyzing a sample in order to produce data corresponding to a set of properties of at least one of the individual components thereof, the properties being selected such that said set of properties is adequate for identifying at least one of said components, said method comprising the steps of:
   subjecting said sample to a plurality of separation processes, the separation processes being adapted to produce a corresponding plurality of different distributions of the sample;
   determining said set of properties of the sample, to produce a corresponding sample set, at each of a plurality of positions along each of said distributions;
   analyzing all of the sample sets corresponding to all of said distributions to determine one or more common basic sets, such that all of the sample sets can be represented by the common basic sets, whereby said common basic sets are estimates of said set of properties for individual components.

13. The method of claim 12, wherein the plurality of separation processes comprises two chromatographic columns having different stationary phases.

14. The method of claim 13, wherein said set of properties comprises the absorbance of electromagnetic radiation at a plurality of wavelengths.

15. The method of claim 12, wherein analyzing all of the sample sets further comprises normalizing each sample set such that it sums to a constant value.

16. The method of claim 15, wherein analyzing all of the sample sets comprises performing a self-modeling curve resolution analysis on said sample sets.

17. The method of claim 16, wherein analyzing all of the sample sets further comprises mean-centering the data corresponding to each of said properties prior to performing the self-modeling curved resolution analysis.

18. An apparatus for analyzing a sample in order to produce data corresponding to a set of properties of at least one of the individual components thereof, the properties being selected such that said set of properties is adequate for identifying at least one of said components, said apparatus comprising:
   (a) a plurality of separation means adapted to produce a corresponding plurality of different distributions of the sample;
   (b) detection means for determining said set of properties of the sample, to produce a corresponding sample set, at each of a plurality of positions along each of said distributions; and
   (c) processing means including:

(i) means for determining one or more basic sets for each separation means, such that all sample sets corresponding to the distribution produced by that separation means can be represented by the basic sets for that separation means; and (ii) means comparing the basic sets for the different separation means with one another to thereby identify one or more common basic sets such that all of the sample sets can be represented by the common basic sets, whereby said common basic sets are estimates of said set of properties for individual components.

19. The apparatus of claim 18, wherein the plurality of separation means comprises two chromatographic columns having different stationary phases.

20. The apparatus of claim 19, wherein the detection means comprises at least one spectrophotometric detector, and wherein said set of properties comprises the absorbance of electromagnetic radiation at a plurality of wavelengths.

21. The apparatus of claim 18, wherein the means for comparing the basic sets comprises means for finding a new basic set such that there exists a plurality of first basic sets such that, for each first basic set, a second basic set not found for any separation means for which said first basic set was found can be represented as a linear combination of said first basic set and said new basic set.

22. The apparatus of claim 18, wherein the means for comparing the basic sets further comprises means for identifying one or more incomplete basic sets found for less than all separation means, and for each incomplete basic set, determining whether said incomplete basic set can be represented as a linear combination of two basic sets not found for any separation means for which said incomplete basic set was found and, if it can be so represented, for each separation means for which said incomplete basic set was found, deleting said incomplete basic set and adding said two basic sets.

23. The apparatus of claim 22, wherein the means for comparing the basic sets comprises means for finding a new basic set such that there exists a plurality of first basic sets such that, for each first basic set, a second basic set not found for any separation means for which said basic set was found can be represented as a linear combination of said first basic set and said new basic set.

24. The apparatus of claim 18, 22, 21 or 23, wherein the means for determining the basic sets for each separation means further comprises means for analyzing, for each group of one or more components fully separated from the other components by that separation means, the sample sets corresponding to said group to determine the number of components in said group and the basic sets for said group, such that all sample sets corresponding to said group can be represented by the basic sets for said group.

25. The apparatus of claim 24, wherein the means for analyzing the sample sets corresponding to said group comprise means for performing a self-modeling curve resolution analysis on the sample sets corresponding to said group such that said group is resolved into one or more basic sets.

26. An apparatus for analyzing a sample in order to produce data corresponding to a set of properties of at least one of the individual components thereof, the properties being selected such that said set of properties is adequate for identifying at least one of said components, said apparatus comprising:

a plurality of separation means adapted to produce a corresponding plurality of different distributions of the sample;

detection means for determining said set of properties of the sample, to produce a corresponding sample set, at each of a plurality of positions along each of said distributions; and processing means including means for analyzing all of the sample sets corresponding to all of said distributions to determine one or more common basic sets, such that all of the sample sets can be arranged by the common basic sets, whereby said common basic sets are estimates of said set of properties for individual components.

27. The apparatus of claim 26, wherein the means for analyzing all of the sample sets comprises means for performing a self-modeling curve resolution analysis on said sample sets.

28. The apparatus of claim 26, wherein the plurality of separation means comprises two chromatographic columns having different stationary phases.

29. The apparatus of claim 28, wherein the detection means comprises at least one spectrophotometric detector, and wherein said set of properties comprises the absorbance of electromagnetic radiation at a plurality of wavelengths.

* * * * *